United States Patent [19]

Bechtel

[11] Patent Number: 4,627,293

[45] Date of Patent: Dec. 9, 1986

[54] APPARATUS FOR TENSION TESTING OF LUMBER

[75] Inventor: Friend K. Bechtel, Moscow, Id.

[73] Assignee: Metriguard, Inc., Pullman, Wash.

[21] Appl. No.: 783,469

[22] Filed: Oct. 3, 1985

[51] Int. Cl.$^4$ ............................................. G01N 3/08
[52] U.S. Cl. ....................................... 73/831; 73/826; 73/859
[58] Field of Search ................. 73/826, 831, 833, 834, 73/856, 859, 860; 269/217, 234; 254/106

[56] References Cited

U.S. PATENT DOCUMENTS

| | | | |
|---|---|---|---|
| 213,586 | 3/1879 | Olsen | 73/859 |
| 2,245,316 | 6/1941 | Amsler | 73/859 |
| 2,583,885 | 1/1952 | Russenberger | 73/860 |
| 3,224,259 | 12/1965 | De Nicola | 73/859 |
| 3,714,820 | 2/1973 | Strickler et al. | 73/826 |
| 4,194,402 | 3/1980 | De Nicola | 73/859 |

FOREIGN PATENT DOCUMENTS 0036039 4/1981 Japan .................................... 73/856

OTHER PUBLICATIONS

Zhulev, "Methods of Increasing the Effectiveness of Test Machine Wedge Clamps", Apr. 1973, Ind. Lab., vol. 39, No. 4, pp. 669-670.

Primary Examiner—Stewart J. Levy
Assistant Examiner—Robert R. Raevis
Attorney, Agent, or Firm—Wells, St. John & Roberts

[57] ABSTRACT

A lumber testing apparatus incorporates opposed wedges to simultaneously exert tension and clamp forces on boards being tested. The inclined wedge surfaces utilize bearing materials and wedge angles selected to match the required clamp forces to tension forces on each board, without crushing the boards at high loads. This is accomplished by using bearing materials having a variable coefficient of friction under varying load conditions.

2 Claims, 11 Drawing Figures

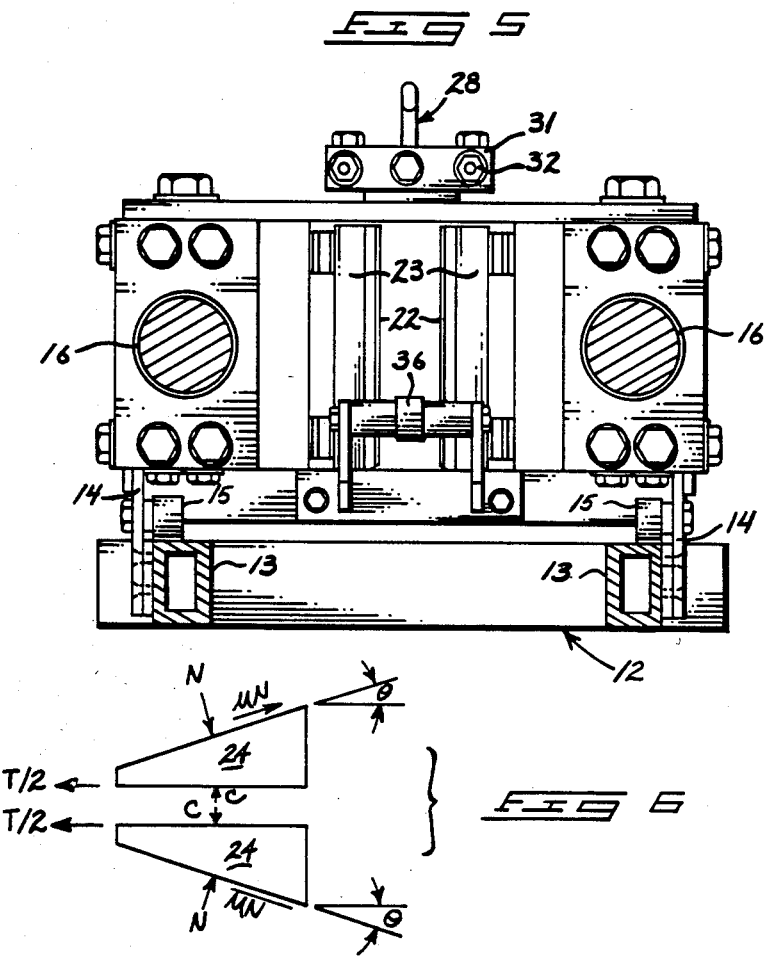
FIG 5
FIG 6
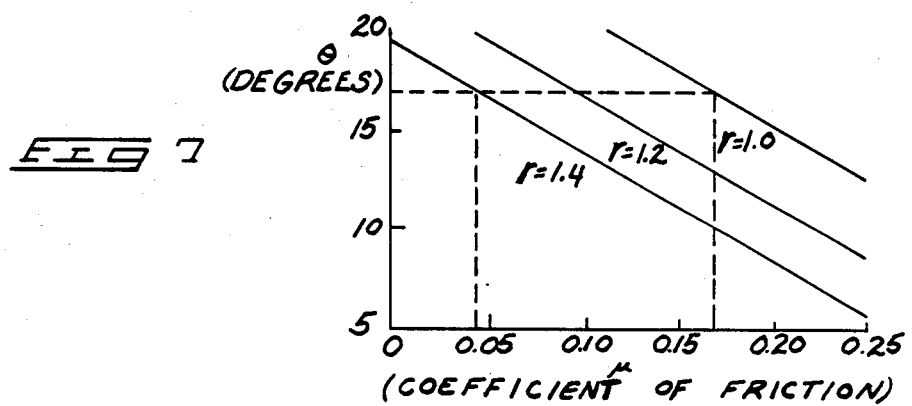
FIG 7

APPARATUS FOR TENSION TESTING OF LUMBER

FIELD OF THE INVENTION

The field of the present invention is testing apparatus for longitudinal strength testing of lumber.

BACKGROUND OF THE INVENTION

Loading lumber to stress levels at some factor above its design value is a useful method for proving its strength. Boards with naturally occurring strength-reducing characteristics such as knots and decay, or with distorted grain or man-made characteristics such as finger joints or machining inaccuracies, if severe enough, can be failed by loading them prior to use. By this method, substandard material can be removed from use, increasing the minimum strength in the population of surviving boards.

Because of lower costs, smaller force, and lack of a clamping requirement, most testing and research of lumber strength properties has been in bending. However, in many cases tension is the preferred strength property to prove or measure. Tension loading offers a more thorough test of all elements of the material cross-section than does bending. There is less risk of testing-induced incipient failures with tension than with bending. This includes the risk of causing compression wrinkles in lumber and the risk of weakening the outer fingers in the joints of horizontally finger-jointed material. In addition, the duration of maximum load is more easily controlled in the production line with tension than with bending test apparatus. In many cases of interest for structural lumber, such as for the lower chords of trusses, tension testing more nearly simulates the actual condition of use.

Any improvement in tension testing apparatus which reduces the cost and eases the clamp complexity will make tension testing more practical and thus bring it into more generally use. Because the clamping mechanism has been the most costly part of tension proof testing apparatus for lumber, it follows that clamp innovation is important.

The present disclosure presents an apparatus for gripping lumber with clamps such that the clamping force is not so high as to crush the material nor so low as to allow slippage when the tensile load is applied. This apparatus can be used for tensile testing of lumber to provide the strength of individual pieces of lumber or wood timers at high tensile loads. Tested material can be used with greater confidence in its reliability for critical structural applications. The tension testing apparatus can also be used for researching the tensile strength of materials and for production quality control testing.

To apply a tensile force to material such as lumber, one must first grip it sufficiently well at two places with clamps. When tensile force is applied, the clamps must not slip along the lumber surfaces. The tensile force that can be applied before slippage occurs is a function of the clamping force and the coefficient of friction at the wood/clamp interface. The condition that must be satisfied is:

$$T < 2C\mu_w$$

where T is the tensile force applied, C is the clamping force applied in the direction perpendicular to the wood/clamp interface, and $\mu_w$ is the coefficient of friction at the wood/clamp interface. The factor "2" enters this relation because there are two wood/clamp interfaces. Also important, when dealing with crushable material such as wood, is its crushing strength, or the amount of clamp pressure the wood material can sustain before it is crushed by the clamps.

For a given tensile force T to be allowed, one must make the friction $\mu_w$ and/or the clamping force C large enough so that the above relation is satisfied. But the clamping force C must not be so large as to cause crushing.

One method used in previous designs for increasing the friction has been to use serrated metal grip plates; then when clamp pressure is applied, the teeth bite into the material surface. U.S. Pat. Nos. 3,556,480, 3,685,801, and 3,763,654 utilize this method for clamping material. Although serrated grip plates greatly increase the effective friction, they also cause damage to the surfaces of the test specimen.

The best clamp gripping surface presently known which does not cause damage to wood but yet has a reasonably high friction against wood is provided by a soft (70–90 durometer) polyurethane coating applied to a steel backing, the polyurethane serving as the gripping interface. The polyurethane-to-wood interface has enough friction to prevent slippage of the grips provided the force C is large enough. But, the range of acceptable forces is limited because crushing of boards will occur if the force is too large.

The acceptable clamp force range can be increased by increasing the clamp contact area. Practically, this is accomplished by increasing the length of the clamps. The tradeoff the length of the material clamped versus the length tested. Also, the larger the clamp area, the more difficult and expensive it is to apply a uniform clamping pressure over this area.

Test specimens of lumber that will sustain the higher tensile loads also will usually sustain higher clamp forces without crushing. Previous clamp designs have made use of this fact by using the same hydraulic pressure to actuate the clamp force that actuates the tensile force in a linear relationship. Then, as the tensile force increases, so also does the clamp force. The clamp force to tensile force ratio is controlled by choice of the actuating hydraulic cylinder areas. This method has proved to be technically acceptable, but it is very expensive because of the hydraulic apparatus required. It has also been observed experimentally with this type of equipment that for the higher tensile forces, the clamp force to tensile force ratio required to prevent slippage increases. To achieve the required ratio at high tensile forces, one must increase the ratio over the entire force range because the hydraulic cylinder areas cannot be adjusted in use.

Another method for achieving a constant clamp force to tensile force ratio uses a mechanical wedge arrangement so that with application of tesnile force, grip plates moving along the inclined planes of wedge members also move perpendicularly to the tensile force direction thereby causing a clamping force. The amount of clamping force is dependent on the angle of the inclined planes, the coefficient of friction between the grip plate/wedge member interfaces, and the tensile force applied. Use of wedges in one form or another can be found in the following U.S. Pat. Nos.: 839,784; 2,831,654; 2,989,337; 3,168,205; 3,170,322; 3,556,480;

3,685,801; 3,763,654; 3,774,352; 3,815,117; 4,050,675; 4,053,255; 4,208,045; 4,365,792; 4,410,169; and 4,506,871. The wedge clamp method for tension testing has been applied to off-line quality control testing of lumber and other wood products. Advantages of the mechanical wedge arrangement are that fewer parts are required, the inclined planes can be segmented and spread out over the gripping surfaces so that the clamp force is distributed over the grip area, the clamps can tolerate partial coverage of their lengths by the material being tested without damaging the clamp parts, and expensive hydraulic equipment is eliminated.

Disadvantages of prior art mechanical wedge clamps have been problems of friction. The lack of consistency of the coefficient of friction between the pressure plate and the indicated plane has caused inconsistency in the clamp force relative to the tensile force. Consequently, either the clamps sometimes slip on the wood, or the inclined plane angle is adjusted for a higher clamp force to tension force ratio than would otherwise be necessary. This in turn leads to wood fiber crushing problems. Another friction problem is that for the materials which have been used in the grip plate/wedge member interface, static friction is greater than dynamic friction. This can lead to clamp lockup at high force levels. When trying to unload the clamps, they can stick, sometimes requiring the use of sledgehammers to open them. When large tensile forces are applied at very low velocity, the resulting large static friction forces can prevent an increment of tensile force from causing a corresponding increment of clamping force. Thus, particularly at high force levels, slippage of wood in the clamps can occur.

The present invention utilizes a multiple split wedge clamping arrangement for tension testing of lumber. This arrangement uses polytetrafluoroethylene (PTFE) bearings between the moving and stationary wedge members to solve the friction problems that have been seen with other wedge clamps used for tension testing. The properties of PTFE bearings as used in the wedge clamps are uniquely matched to the clamping requirements of lumber provided that the bearing wedge angle and clamp area are properly chosen.

The objective of the invention is to provide a low cost, high reliable, low maintenance clamp apparatus for tension testing of lumber. Lumber can be crushed if subjected to too much clamp pressure, but will slip in the clamps if the clamping pressure and/or the coefficient of friction of the gripping surface against the wood is not sufficiently high.

Although PTFE sliding against steel has a relatively large coefficient of friction when compared with roller or ball bearings, its reduced coefficient of friction with increased load, its static values that are no higher than its dynamic friction values, and the designer's ability to choose its sliding contact bearing load area and wedge angle make PTFE an ideal solution as the bearing material between relatively moving wedge members in this application. Further, PTFE is a low cost solution and its natural viscoelastic deformation characteristics under load allow it to conform to manufacturing tolerances of less precision than are required for rolling bearings. The method described for computing bearing area causes large bearing pressures at rated tension load for the clamps. This is the minimum coefficient of friction situation and is shown to correspond to a maximum clamp-to-tension force ratio. Experimentally, higher clamp-to-tension force ratios are needed at high loads than at low loads to prevent slippage of lumber. The decreasing coefficient of friction with increasing load makes PTFE an ideal choice of bearing material to match the clamping force versus load requirements of lumber. Such matching requires proper choice of both bearing area and wedge angle according to the described procedure.

Another advantage of the wedge clamp apparatus with PTFE bearings is the absence of clamp lockup. Clamp lockup occurs as a result of "stiction" which occurs when the static coefficient of friction for a bearing material is larger than its dynamic coefficient of friction. Practically all bearing materials except PTFE exhibit some stiction.

Use of wedge clamps is more efficient in the production-line tension testing of lumber than the use of hydraulic clamps. For fast operation, hydraulic clamps need a separate low pressure, high flow hydraulic circuit for fast clamp action until the clamps contact the wood; then it is necessary to switch to high pressure and low flow. Accumulators, valving and controls to accomplish this are complex and expensive when compared to the simplicity of using an air cylinder or other simple low cost actuator for the "close" and "open" functions of the wedge clamping apparatus.

BRIEF DESCRIPTION OF DRAWINGS

FIG. 5 is a sectional view taken along line 5—5 in FIG. 2;
FIG. 6 is a diagrammatic free body diagram of the movable wedges of one clamp;
FIG. 7 is a plot of wedge angle versus bearing coefficient of friction for clamp to tension force ratios of 1.0, 1.2, and 1.4.

DESCRIPTION OF THE PREFERRED EMBODIMENT

Figure 1:
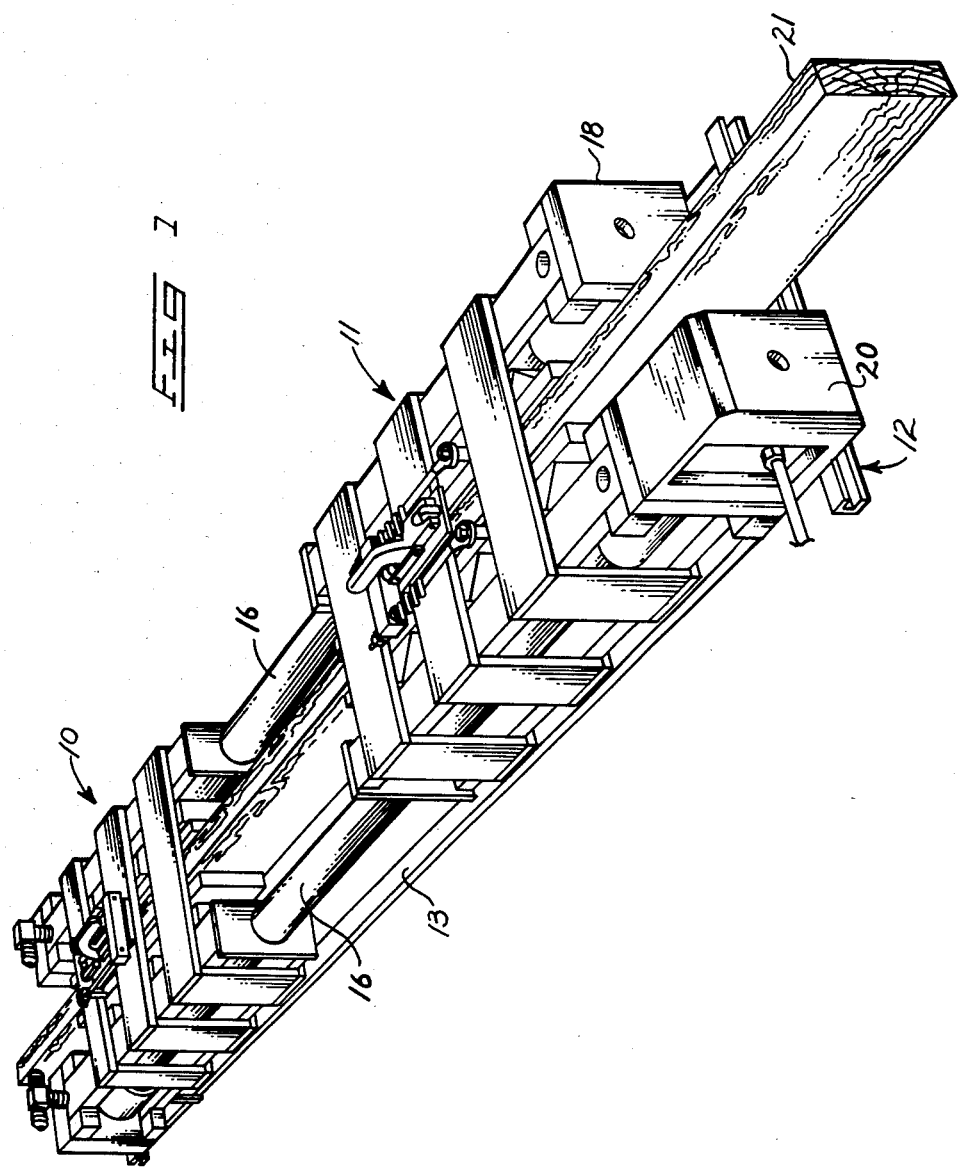
FIG. 1 is a perspective view of the testing apparatus.
Figure 2:
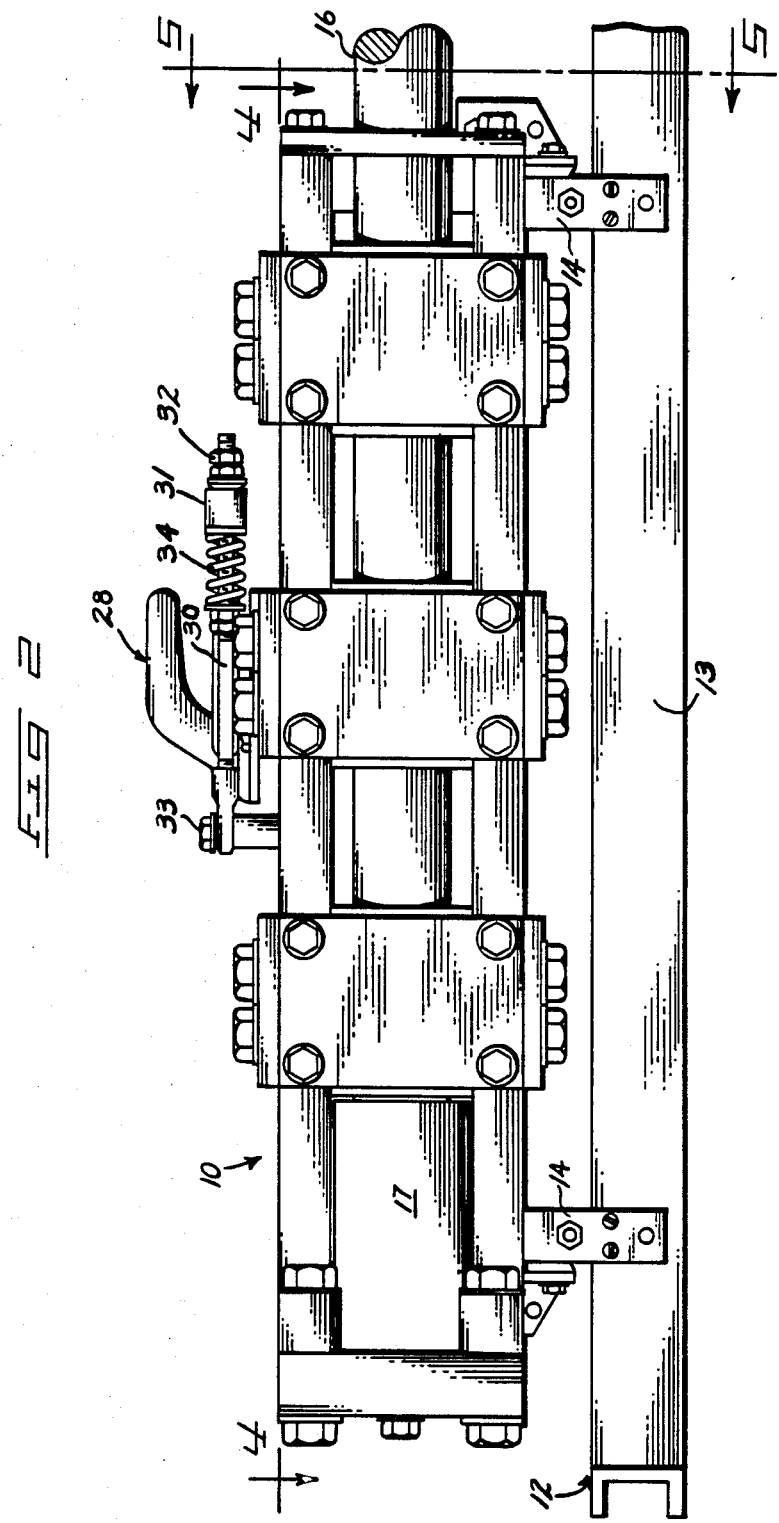
FIG. 2 is an enlarged side elevation view of one end of the testing apparatus.
Figure 3:
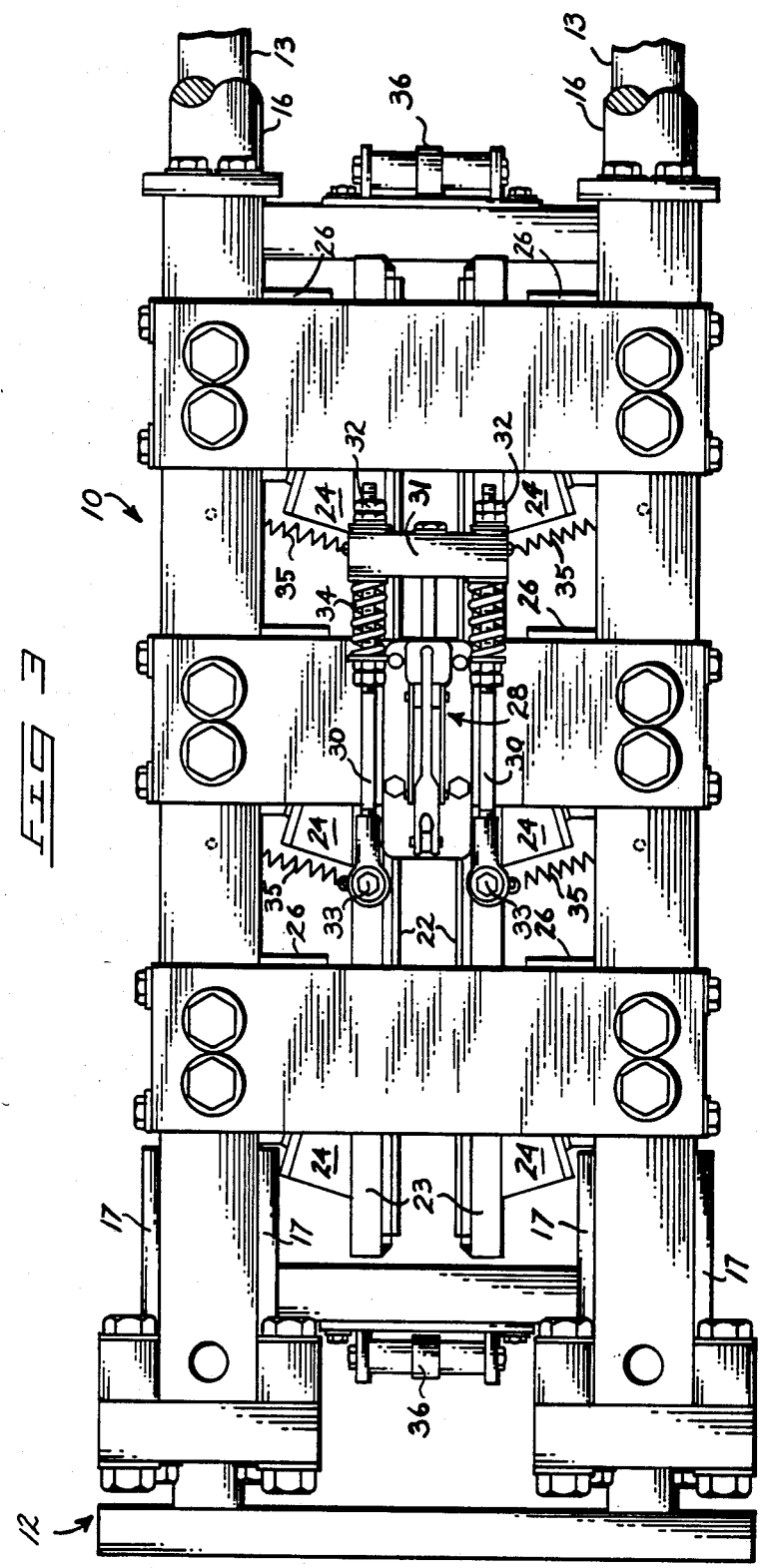
FIG. 3 is a top view of FIG. 2.
Figure 4:
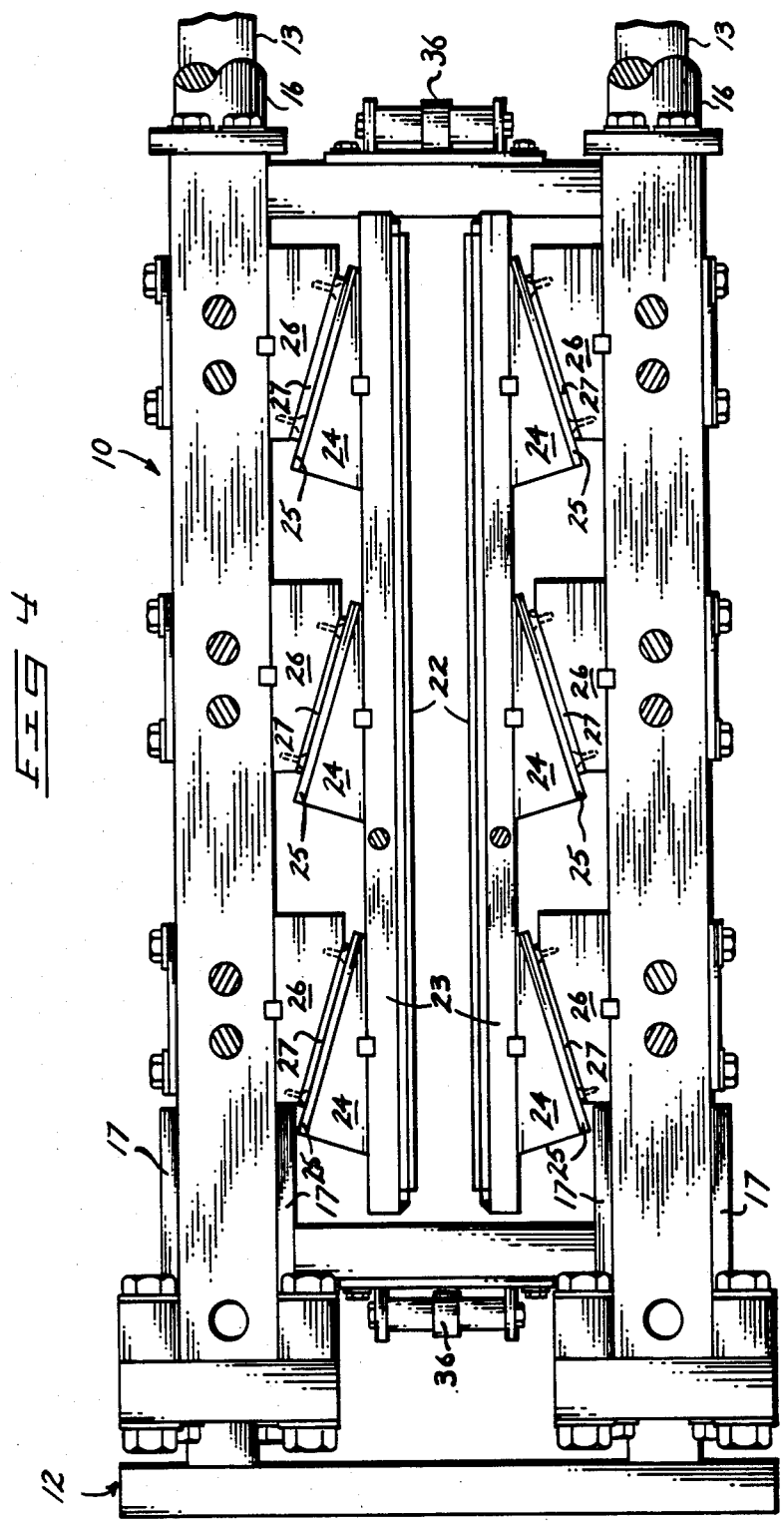
FIG. 4 is a sectional view taken along line 4—4 in FIG. 2.

In compliance with the constitutional purpose of the Patent Laws "to promote the progress of science and useful arts" (Article 1, Section 8), applicant submits the following disclosure of the invention.

FIGS. 1-5 illustrate a preferred embodiment of the wedge clamp apparatus. FIGS. 1-5 show the important parts of the clamps as configured for tension testing of individual lengths of lumber in a laboratory application. It is clear that, with minimal modification and additions, the same apparatus can be used for automatic production-line testing. For example, the hand-operated toggle mechanism for initial clamp closing could be replaced with an air or electric powered actuator. The illustrated frame could also be modified to allow lateral entry and exit to or from the clamps instead of the endwise entry and exit illustrated in FIG. 1. Neither the initial clamp closing mechanism nor the entry and exit plan affects the important wedge and wedge bearing features of the wedge clamp apparatus.

In the illustrated apparatus, a pair of opposed clamp frames 10 and 11 are independently movably guided on longitudinal rails 13 of a stationary base frame 12. Frames 10 and 11 are transversely guided by outer vertical bearing pltes 14 which slide along the outside surfaces of the respective rails 13. The weight of frames 10 and 11 is supported by rollers 15 that engage the upper surfaces of the rails 13 (FIG. 5).

The clamp frames 10 amd 11 are longitudinally joined to one another by two push rods 16 that extend between their respective outer ends. Clamp frame 10 is connected to one end of each push rod 16 by means of interposed cylinder assemblies 17. Clamp frame 11 is connected to the remaining end of one push rod 16 by a transverse load plate 18 and to the remaining end of the other push rod 16 by a load cell assembly 20. The load cell assembly 20, of conventional design, can be used for electronically measuring the forces between the push rods 16 and clamp frames 10 and 11 for testing purposes. The cylinder assemblies 17 utilize hydraulic pressure to exert force between the outer end of frame 10 and the connected ends of the push rods 16. This force, when transferred to the push rods 16 and the outer end of the reactive clamp frame 11, tends to urge the movable clamp frames 10 and 11 apart from one another with respect to the supporting base frame 12. The force can be applied between the clamp frames 10 and 11 as a tensile force exerted on a test board 21 clamped to each of the frames 10 and 11. In this manner, the longitudinal strength of board 21 can be measured by tension testing techniques.

The clamp assemblies included on the two clamp frames 10 and 11 are constructed as mirror images of one another. Although FIGS. 2-5 show the clamp assembly on frame 10, it is to be understood that identical elements are provided within clamp frame 11.

Referring to FIGS. 2-5, the clamp assembly includes rectangular grip plates 22 which engage opposite side surfaces of each board 21 being tested. Grip plates 22 are preferably smooth surfaced plates having sufficient area to assure that the boards 21 are gripped without crushing during the projected range of tensile loading. In a preferred embodiment, the grip plates 22 have opposed surfaces coated with 70-90 durometer polurethane.

The relatively thin grip plates 22 are backed by longitudinal pressure plates 23. Each pressure plate 23 has a series of wedges 24 fixed to its back surface. Steel wear plates 25 are secured to the inclined surfaces of the movable wedges 24.

Clamp frame 10 has a series of wedges 26 fixed to it in opposition to the wedges 24. The complementary inclined surfaces of the wedges 26 are coated with PTFE bearing material 27. Because PTFE exhibits cold-flow characteristics under load, the preferred bearing material uses PTFE combined with another material as a backing. Examples of such materials are listed below.

Initial clamping pressure against the side surfaces of a board 21 is applied mechanically through a toggle mechanism 28 mounted on clamp frame 10. The toggle mechanism 28 is used to manually displace the pressure plates 23 relative to clamp frame 10. Manual operation of a handle (shown in locked position) shifts a transverse set bar 31 relative to frame 10. Bar 31 moves to the right, or inwardly, when locked; and to the left, or outwardly, when released. A pair of drag links 30 freely extend through set bar 31. Adjustable nuts 32 threaded to one end of each drag link 30 abut against set bar 31. The remaining ends of the drag links 30 are coupled to the pressure plates 23 by upstanding bolts 33. When bar 31 is shifted inwardly by the handle and toggle mechanism 28, it pulls the drag links with it, applying initial clamping force to pressure plates 23. Preloaded compression springs 34 are interposed between the drag links 30 and the back side of set bar 31 to accommodate further movement between pressure plates 23 and clamp frame 10 during tension testing of a board. Compression springs 34 also exert releasing forces between clamp frame 10 and the pressure plates 23 to back the pressure plates 23 along the wedges and separate them from the board after testing has been completed.

Pressure plates 23 are yieldably held on clamp frame 10 by inclined tension springs 35. The light pressure of springs 35 holds wedges 24 on the wedges 26 when the toggle mechanism 28 is released.

Clamp frame 10 is provided with a pair of transverse rollers 36 which support and guide individual boards fed longitudinally between the pressure plates 23.

When a board is to be tested, it is moved longitudinally through the clamp frames 10 and 11 on the rollers 36. The side surfaces of the board 21 are then initially engaged between the grip plates 22 by mechanical actuation of toggle mechanism 38. The purpose of toggle mechanism 28 is to preload the wedges 24 and 26 to thereby establish frictional contact between the surfaces of grip plates 22 and the opposed surfaces of the board 21.

After each board 21 is initially clamped, the cylinder assemblies 17 can be hydraulically actuated to urge the two clamp frames 10 and 11 apart from one another. Due to the action of the inclined surfaces between wedges 24 and 26, the tensile force applied to each board 21 will result in application of clamping forces to the board 21. The clamping force will increase in magnitude as the tensile force applied to a particular board is increased. Thus, stronger boards will have greater clamping forces exerted on them, assuring that no slippage occurs at higher tensile loads. As explained below, the increase in clamping force is preferably non-linear.

FIG. 6 is a diagrammatic free body diagram of the movable wedge member 24 of one clamp assembly and illustrates the forces acting on these members. N is the force normal to the inclined plane of the movable wedge surfaces. T is the tension force applied to a board. C is the clamping force applied to the board. $\mu$ is the coefficient of friction for the bearing material 27 sliding on the wear plates 25. The retarding friction force along the opposed inclined surfaces of wedge 24 is therefore $\mu N$.

Summing forces first in the direction of tension and then in the direction of clamping yields the relationship:

$$\theta = \tan^{-1}[(1-2r\mu)/(2r+\mu)] \quad (1)$$

where $\theta$ is the wedge angle for both the stationary and movable wedges 26, 24, and $r=C/T$ (the ratio of clamp-to-tension forces).

FIG. 7 is a plot of calculations for wedge angle $\theta$ versus bearing coefficient of friction $\mu$ for a range of clamp-to-tension force ratios r of 1.0, 1.2, and 1.4 derived from Equation (1). Experience with tension testing of lumber indicates that with polymer coated grip plates 22, a clamp-to-tension force ratio of 1.0 is adequate to prevent slippage for low tension forces, whereas 1.4 might be required for high tension forces. FIG. 7 shows that for a wedge angle $\theta$ of 17°, mathematically derived values for the clamp-to-tension forces ratio r vary from 1.0 to 1.4 as the coefficient of friction $\mu$ varies from 0.17 to 0.045 (see horizontal dashed line). This range of friction coefficients also fits the published range of values for commercially available PTFE bearing materials that are lightly to heavily loaded. Consequently, when PTFE bearing materials are used along the inclined surface of wedges 24, 26 at an inclined angle of 17°, the clamp-to-tension force ratio r for low tension forces will be approximately 1.0, whereas for high forces, it will be approximately 1.4.

Solving Equation (1) for clamp-to-tension force ratio r gives:

$$r = 0.5(1 - \mu \tan \theta)/(\mu + \tan \theta) \quad (2)$$

Figure 8:
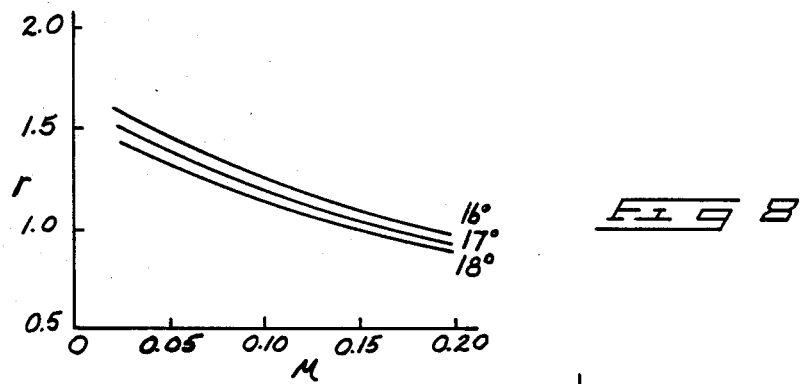
FIG. 8 is a plot of clamp to tension force ratio versus bearing coefficient of friction for the three wedge angles 16°, 17°, and 18°.

FIG. 8 is a plot of r versus bearing coefficient of friction $\mu$ for the three wedge angles 16°, 17°, and 18° using PTFE bearing materials on the inclined surfaces. These curves illustrate the influence of wedge angle on the ratio r.

Figure 9:
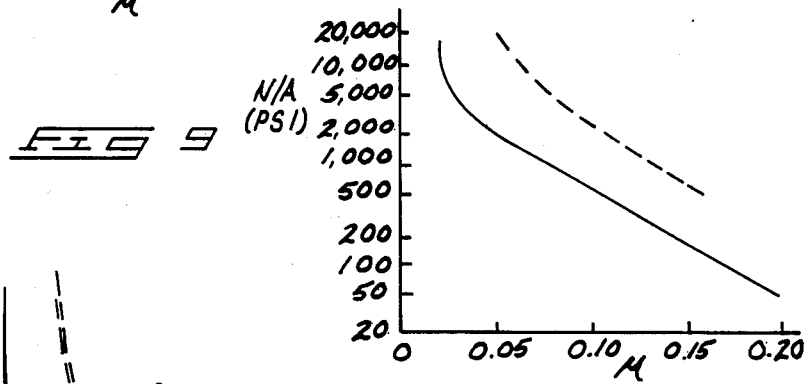
FIG. 9 is a plot of per unit bearing load versus coefficient of friction for PTFE material from two manufacturers' published data.

Once can write the clamp force C as:

$$\begin{aligned} C &= N(\cos\theta - \mu\sin\theta) \quad (3) \\ &= A(N/A)(\cos\theta - \mu\sin\theta) \\ &= Af(\mu)(\cos\theta - \mu\sin\theta) \end{aligned}$$

where A is the total bearing area of one side of the clamps and $f(\mu) = N/A$ which defines the functional relationship between coefficient of friction and per unit bearing load. FIG. 9 is a plot of per unit bearing load $N/A = f(\mu)$ versus coefficient of friction $\mu$ for two PTFE bearing materials available from manufacturers' published data. The two materials are distinguishable in FIGS. 9-11, where values relating to one are shown by solid curves and values relating to the other are shown by broken line curves.

Dividing both sides of Equation (3) by T gives:

$$r = C/T = Af(\mu)(\cos\theta - \mu\sin\theta)/T$$

or, solving for T/A:

$$T/A = f(\mu)(\cos\theta - \mu\sin\theta)/r \quad (4)$$

Figure 10:
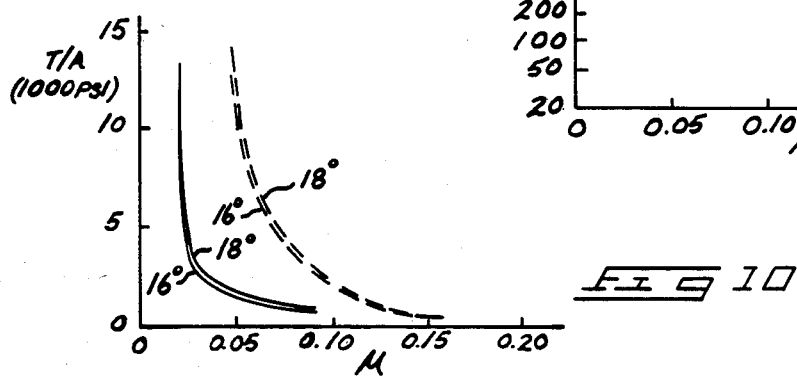
FIG. 10 illustrates the ratio of tensile force to bearing area versus bearing coefficient of friction for the PTFE bearing material from the manufacturers' data represented in FIG. 9.
Figure 11:
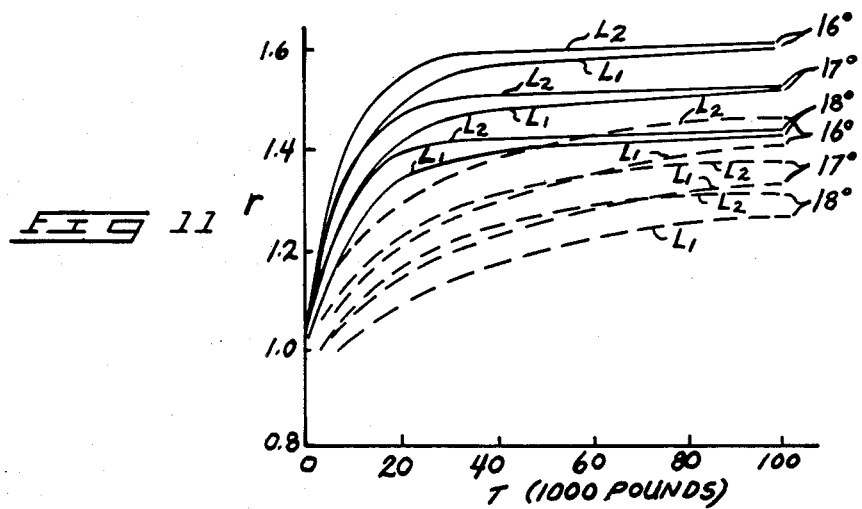
FIG. 11 is a plot of clamp to tension force ratio versus tension force for wedge angles 16°, 17°, and 18°.

Utilizing FIG. 8 and FIG. 9 for r and N/A rspectively, FIG. 10 is a plot of T/A versus $\mu$ as computed from Equation 4. The plot of r versus T in FIG. 11 is obtained by computing r from Equation (2) and $T=(T/A)A$ where T/A is obtained from Equation (4). In FIG. 11, the bearing area A has been adjusted to give alternative maximum per unit bearing loads of 10,000 psi ($L_1$) and 20,000 psi ($L_2$).

It is clear from FIG. 11 that r increases with T, but at varying rates. Further, the amount of increase can be adjusted by choosing the wedge angle $\theta$ and the maximum per unit bearing load N/A.

The preferred embodiment of this invention incorporates bearing areas and wedge angles along the inclined bearing surfaces determined by the following design steps to meet lumber loading requirements without crushing of tested boards:

1. Select a PTFE bearing material whose coefficient of friction decreases with load and whose static friction is not greater than its dynamic friction. Two actual PTFE materials which have been used for this purpose are DU Self-lubricating bearing material (Garlock Bearings, Inc., of Thorofare, N.J.) and Duralon bearing material (Rexnord, Inc., of Downer's Grove, Ill.).
2. From the manufacturer's published data, per unit bearing load over a selected range of values can be related to the varying coefficient of friction of the selected bearing material. This can be done by tabulating or plotting the functional relationship $f(\mu) = N/A$, for example see FIG. 9. The ratio of clamp-to-tension forces over a selected range of values can be related to the coefficient of friction for selected wedge angles.
3. One can utilize Equation (2) and/or FIG. 8 to define the relationship of r versus $\mu$ for particular wedge angles.
4. Next, the ratio of tension force to area of bearing material over a selected range of values can be related to the coefficient of friction for the selected bearing material. This can be done by using Equation (4) and data from Steps 2 and 3, to compute and plot T/A versus $\mu$ for particular wedge angles and materials, for example see FIG. 10.
5. For the PTFE material selected in Step 1, one can then arbitrarily select a maximum per unit bearing load within the selected bearing material specifications, note its corresponding coefficient of friction value from Step 2, and obtain the corresponding ratio of tension force to area of bearing material (T/A), using data from Step 4. By dividing the desired maximum tensile load by T/A, one can obtain the bearing area A for one side of the clamps.
6. For each coefficient of friction in the range of values for the PTFE material chosen in Step 1, each bearing area obtained from Step 5, and each selected wedge angle, one can compute r from Equation (2) and $T=(T/A)A$ where T/A is obtained from Equation (4). Then one can relate the ratio of clamp-to-tension forces to tension force for the selected wedge angles by plotting r versus T (see FIG. 11).
7. From the above information, one can select a wedge angle, using data from step 6, to maintain a relationship between the ratio of clamp-to-tension forces and tension force over a range of tension forces extending to the preselected maximum tensile forces such that the resulting clamp forces per unit area across the grip plates 22 do not exceed the known crushing strength of the boards being tested. This can be done by plotting r versus T for various wedge angles (FIG. 11) and comparing the resulting curves for the wedge angles $\theta$ and the bearing area A (determined from the selected maximum per unit bearing load, see Step 5) to identify the best available match for the desired curve of r versus T.

FIG. 11 illustrates the result of this procedure for two available PTFE bearing materials, wedge angles of 16°, 17°, and 18°, and maximum bearing loads of 10,000 and 20,000 psi, which are labeled as $L_1$ and $L_2$ respectively. Note from FIG. 11 that increasing the wedge angle $\theta$ and increasing the bearing area A both decrease the ratio r. As a result, the ratio of clamp-to-tension force will be increased in a non-linear manner at a decreasing rate as the tensile force applied to a board is increased. This provides the high clamp force levels needed for testing of high strength boards, while reducing clamping forces on low strength boards below levels ordinarily encountered when using clamps having a constant clamp-to-tension rate.

This design process can be done manually, as described, or can be accomplished by a properly programmed computer, using available data for bearing materials and lumber being tested.

Selection of a bearing material without stiction is of importance in the design of this clamp assembly for two reasons. First, since the coefficient of static friction does not exceed the dynamic coefficient of friction, reversal can take place smoothly without locking of the clamps. This reversal occurs at the end of each testing cycle. When hydraulic pressure to cylinder assemblies 17 is released, the cylinders return springs will retract the clamps as the clamp frames 10 and 11 are moved toward one another by the push rods 16. Secondly, at the very low speeds of relative movement along the inclined surfaces of wedges 24 and 26, the absence of stiction assures a smooth, predictable increase in clamp force as tension force on a board increases. If stiction exists, such increases would lead to erratic relative motion between the wedges 24 and 26, because the speeds involved are so low that they bridge the borderline between static and dynamic friction conditions.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, threfore, claimed in any of its forms or modifications within the proper scope of the appended claims, appropriately interpreted in accordance with the doctrine of equvalents.

I claim:

1. An apparatus for longitudinal strength testing of lumber, comprising:
   grip plate means for engaging opposite surfaces of a board at two longitudinally spaced locations along its length;
   force means operably connected to the grip plate means for selectively applying a progressively increasing longitudinal tensile force to the board engaged thereby in a direction parallel to its engaged surfaces;
   wedge means interposed between said force means and said grip plate means for applying a transverse clamping force to the grip plates that varies as a function of the tensile force applied to the board engaged by said grip plate means;
   said wedge means includes an inclined bearing surface area of polytetrafluoroethylene sliding against steel arranged at a wedge angle relative to the engaged surfaces of the board between relatively movable elements operably connected to said force means and to said grip plate means respectively, said inclined bearing surface area having a coefficient of friction that progressively decreases with increasing load in a direction normal to the inclined bearing surface area as tensile force is applied to the board engaged by said grip plate means, to progressively increase the ratio of the clamping force to the tensile force in a non-linear manner at a decreasing rate as the tensile force applied to the board is increased.

2. The apparatus of claim 1, wherein the bearing surface area and wedge angle for the wedge means are determined by the following steps:
   (1) relate per unit bearing load (N/A) over a selected range of values, and expressed as the ratio of the force normal to the bearing surface area (N) to the bearing surface area (A), to the coefficient of friction ($\mu$) for a selected bearing material;
   (2) relate the ratio of clamp-to-tension forces (C/T) over a selected range of values to the coefficient of friction ($\mu$) for selected wedge angles ($\theta$);
   (3) relate the ratio of tension force to area of bearing material (T/A) over a selected range of values to the coefficient of friction ($\mu$) for the selected bearing material using data obtained from Steps 1 and 2;
   (4) arbitrarily selected a maximum per unit bearing load (N/A) within the known specifications for the selected bearing material, determine its corresponding coefficient of friction ($\mu$) from Step 1 and obtain the corresponding ratio of tension force to area of bearing material (T/A), using data from Step 3;
   (5) divide a preselected maximum tensile force (T) by the ratio of tension force to area of bearing material (T/A) at the maximum per unit bearing load (N/A) obtained in Step 4 to obtain the bearing area (A);
   (6) relate the ratio of claim-to-tension forces (C/T) to tension force (T) for selected wedge angles ($\theta$), using data from Steps 4 and 5; and
   (7) select a wedge angle ($\theta$) using data from Step 6, to maintain a relationship between the ratio of clamp-to-tension forces (C/T) and tension force (T) over tension forces extending to the preselected maximum tensile forces such that the resulting clamp forces per unit area of said grip plate means do not exceed the crushing strength of the board being tested.

* * * * *